United States Patent [19]

Kobayashi et al.

[11] Patent Number: 4,673,807

[45] Date of Patent: Jun. 16, 1987

[54] AUTOMATIC RANGE CONTROL METHOD FOR AN OPTICAL DENSITY/DOT PERCENTAGE MEASURING DEVICE

[75] Inventors: Yuji Kobayashi, Ageo; Norio Takahashi, Tokyo, both of Japan

[73] Assignee: Dai Nippon Insatso Kabushiki Kaisha, Japan

[21] Appl. No.: 785,503

[22] Filed: Oct. 8, 1985

[30] Foreign Application Priority Data

| Oct. 12, 1984 | [JP] | Japan | 59-153809[U] |
| Nov. 2, 1984 | [JP] | Japan | 59-230399 |
| Nov. 2, 1984 | [JP] | Japan | 59-230400 |
| Nov. 2, 1984 | [JP] | Japan | 59-230401 |

[51] Int. Cl.$^4$ .................... H01J 40/14; G01N 21/00
[52] U.S. Cl. ........................... 250/214 AG; 356/443
[58] Field of Search ............ 250/206, 214 AG, 214 R, 250/559; 356/379, 380, 443, 445; 330/282

[56] References Cited

U.S. PATENT DOCUMENTS

| 4,133,008 | 1/1979 | Tisue .................. 250/214 AG X |
| 4,426,624 | 1/1984 | Beauducel et al. .............. 330/282 X |
| 4,435,679 | 3/1984 | Bedard ...................... 330/282 X |
| 4,574,249 | 3/1986 | Williams .................. 250/214 AG X |

*Primary Examiner*—Eugene R. LaRoche
*Assistant Examiner*—David Mis
*Attorney, Agent, or Firm*—Parkhurst and Oliff

[57] ABSTRACT

This invention relates to an automatic range control method for a compact and portable optical density/dot percentage measuring device which can use a conventional light table as its light source, and which can digitally display a result of measurement. In the method, information obtained from an A/D converter, which converts a measured analog signal to a digital signal, is positively employed for reducing overall measuring time. An A/D conversion is first made at x1 range by a 10 bit A/D converter. The A/D conversion value is compared with predetermined values to determine a gain to be selected and perform further A/D conversion.

9 Claims, 10 Drawing Figures

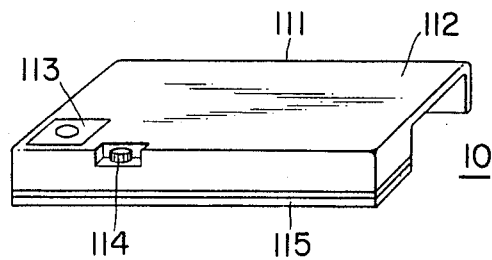
FIG. 7(a)
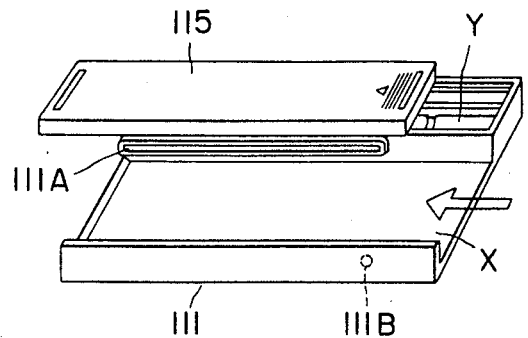
FIG. 7(b)
FIG. 8
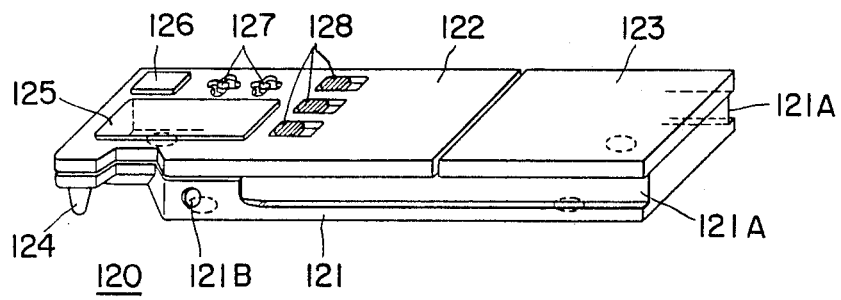
FIG. 9
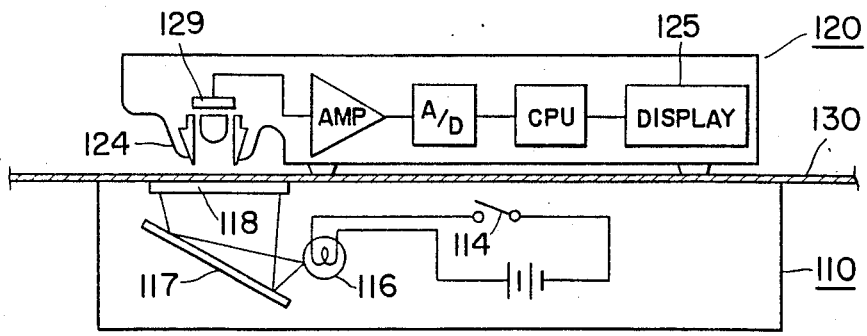

AUTOMATIC RANGE CONTROL METHOD FOR AN OPTICAL DENSITY/DOT PERCENTAGE MEASURING DEVICE

BACKGROUND OF THE INVENTION

1. Technical Field of the Invention

This invention relates to an automatic range control method for a compact and portable optical density/dot percentage measuring device which can use an ordinary light table as its light source, digitally display a result of measurement, and has a high precision in measurement.

2. Prior Art of the Invention and its Technical Problems

An optical density meter is an instrument which detects and displays the intensities of a light source for irradiating a specimen and a transmitted or reflected light from the specimen. In general, the light transmitted from a specimen is converted into an electrical signal by a photoelectric conversion element. The electrical signal is then converted into a density value by either an analog means, or by a digital means such as a microcomputer after the electrical signal is converted from an analog signal into a digital signal. The density value is thereafter displayed. A dot percentage meter is an instrument which measures a gradation (collective density) reproduced from a change in dot areas, based upon the measurement of transmittance or reflectance of a specimen to be measured. Optical density meters and dot percentage meters may be used in common if a different calculation method for display values is used for the respective meters. First, an optical density meter will be explained and thereafter a dot percentage meter will be explained. It is necessary for an optical density meter to measure the quantity of light over a wide optical density range. Therefore, a programmable gain amplifier is provided between a photoelectric conversion element and an A/D converter to amplify a small input signal and thereafter convert the amplified analog signal into a digital signal. This is one of the methods to ensure the precision of A/D conversion.

FIG. 4 is a block diagram showing an example of such an optical density measuring device. A system using a sensor, programmable gain amplifier, A/D converter and microcomputer has been well known in the art. For instance, there is known an SBC711 A/D converter board manufactured by Intel Corp. A system using the SBC711 A/D converter board comprises an analog multiplexer, programmable gain amplifier, sample/hold circuit, A/D converter and CPU. By removing the analog multiplexer and sample/hold circuit and adding a light source, photoelectric conversion element 11, pre-amplifier 12 and display 16, a conventional optical density measuring device as shown in FIG. 4 can be constructed by using the above system available in the market. Assume that the density measuring range of the optical density measuring device constructed as above is 0.0 to 4.0, the gain switching range of the programmable gain amplifier 13 becomes ×1 to ×1000. With such a wide range of gain switching, usually an off-set output voltage of the preamplifier 12 is also amplified at the gain amplifier 13. Therefore, to ensure a highly precise measurement, the preamplifier 12 is needed to be of a high precision thereby resulting in an expensive preamplifier 12.

FIG. 5 is a circuit diagram showing an example of a conventional range switching circuit. The above-mentioned disadvantage of the optical density measuring device is also related to a disadvantage accompanied by an illuminometer while its range is switched. One of the known methods to solve this problem is to use the range switching circuit of FIG. 5, which is disclosed in "Practical Electronic Circuit Handbook" (Published October, 1975, by CQ Publishing Co., Ltd.). The range switching of the circuit is performed by changing the value of a feedback resistor 17 of a preamplifier 12 by means of a range switch 18, without amplifying an off-set voltage of the preamplifier 12. However, a bias current of the preamplifier 12 is amplified so that an amplifier having input FET transistors and a small bias current should be used as the preamplifier 12.

FIG. 6 is a circuit diagram showing an example of a conventional optical density measuring device to which the range switching circuit shown in FIG. 5 is applied. This conventional device is the optical density meter disclosed in Japanese Unexamined Patent Publication No. 56-79946, which comprises a photoelectric conversion element 11, operational amplifier 19, A/D converter 20, operation processing circuit 21, display 22, feedback resistor group 23 (23a to 23d) and analog switch group 24 (24a to 24d). In this case, however, an analog switch is not ideal but has a leakage current even at an off state and produces some error in measurement. This error in measurement essentially increases in proportion to the number of switches. In order to reduce the error in measurement, an analog switch having an ideal characteristic is needed which has no leakage current and zero on-resistance as well as infinite off-resistance. To this end, however, it is necessary to use an expensive analog switch. As a result, the number of analog switches used with an optical density measuring device should preferably be as small as possible in view of improvement on measuring precision, miniaturization and low cost of the circuit.

Apart from the above problems, most of conventional optical density/dot percentage meters have been of a fixed mount type and used a stable light source whose flicker or variation can be neglected by using a light source such as a halogen lamp powered with a stabilized power source. Therefore, those conventional meters are not suitable for using a common commercial light table as their light source and cannot be used as portable optical density measuring devices or dot percentage measuring devices because of a large number of circuit elements and large outer dimension.

Of the dot percentage measuring devices of this type, there is known a dot percentage measuring meter developed by the present applicant aiming at measuring a dot percentage of such as a print original film, which is shown in FIG. 9. This meter has been developed in place of the conventional fixed mount type meter and is featured by its compact and portable nature. This dot percentage meter can accordingly be used for measurement at any location so long as a light table is available.

However, since the light table is fixedly mounted, the dot percentage meter cannot always make the best use of its portable nature and the location of measurement is limited.

OBJECTS OF THE INVENTION

An object of the invention is to provide an efficient range switching method for a portable optical density/dot percentage measuring device which can use as its light source a common light table, obtain a highly precise measurement even under the conditions of light source flicker due to commercial power frequency or light quantity variation due to a change of location, and reduce the number of components.

Another object of the present invention is to provide a compact light source device suitable for use in combination with a portable type dot percentage meter.

SUMMARY OF THE INVENTION

In the portable optical density/dot percentage measuring device according to the present invention, the provision of a low-pass filter and a specific automatic measurement control device enables to use a common light table as its light source. The automatic measurement range control method of the present invention enables to reduce the number of measurement range switchings and shorten the overall measurement time. Therefore, the variation in light quantity caused by a change of measuring location can be readily compensated, the delay of response time can be recovered due to the provision of a low-pass filter, and the number of components can be reduced.

According to one aspect of the present invention, an automatic range control method for an optical density/dot percentage measuring device comprises: a photoelectric conversion element for photoelectrically converting a transmitted or reflected light of an object to be measured into a photocurrent; an operational amplifier for converting said photocurrent into a voltage signal for amplifying said voltage signal; a low-pass filter for cutting off an AC component of said voltage signal from said operational amplifier; an A/D converter for converting said voltage signal from said low-pass filter from an analog value into a digital value; an operation control unit for outputting, in response to said digital signal, switch control signals for the control of the on/off state of a plurality of analog switches and display data; and a gain switching circuit having a plurality of feedback resistors and analog switches connected between the input and output terminals of said operational amplifier for switching a measurement range; wherein said operation control unit outputs said switch control signals to said gain switching circuit in such a manner that said operation control unit calculates a value $Ii=-Vi/Gi$ based upon a value Vi obtained through A/D conversion of a measured value at a given gain Gi, selects a gain $Gi+1$ based upon which one of a plurality of predetermined ranges corresponding to said value Ii; and if the gain $Gi+1$ coincides with the current gain Gi, said value Ii is made an ultimate measured value, while if the gain $Gi+1$ does not coincide with the current gain Gi, then a value $Vi+1$ is obtained through an A/D conversion of the measured value at the gain $Gi+1$ to calculate a value $Ii+1=(Vi+1)/(Gi+1)$, and the similar procedures are repeated until a coincidence is obtained.

According to another aspect of the present invention, an optical density/dot percentage measuring device comprises: a photoelectric conversion element for photoelectrically converting a transmitted or reflected light of an object to be measured into a photocurrent; an operational amplifier for converting said photocurrent into a voltage signal for amplifying said voltage signal; a low-pass filter for cutting off an AC component of said voltage signal from said operational amplifier; an A/D converter for converting said voltage signal from said low-pass filter from an analog value into a digital value; an operation control unit for outputting, in response to said digital signal, switch control signals for the control of the on/off state of a plurality of analog switches and a data signal representative of data to be displayed; a display for displaying said data; and a gain switching circuit having a plurality of feedback resistors connected in parallel between the input and output terminals of said operational amplifier, said analog switches being respectively connected to said feedback resistors except that resister having the largest resistance value.

According to a further aspect of the present invention, an optical density/dot percentage measuring device comprises: a photoelectric conversion element for photoelectrically converting a transmitted or reflected light of an object to be measured into a photocurrent; an operational amplifier for converting said photocurrent into a voltage signal for amplifying said voltage signal; a low-pass filter for cutting off an AC component of said voltage signal from said operational amplifier; an A/D converter for converting said voltage signal from said low-pass filter from an analog value into a digital value; an operation control unit for outputting, in response to said digital signal, switch control signals for the control of the "on/off" state of a plurality of analog switches and a data signal representative of data to be displayed; a display for displaying said data; and a gain switching circuit having a plurality of feedback resistors connected in series between the input and output terminals of said operational amplifier, said analog switches being respectively connected between the terminals of said feedback resistors except that connected to the input terminal of said operational amplifier, and the output terminal of said operational amplifier.

According to another aspect of the present invention, a compact light source device is of a measurement table shape, has at its one corner an illumination section, and is formed on the rear side thereof with a housing capable of fully accommodating a dot percentage meter whose casing couples in engagement with the light source device.

BRIEF DESCRIPTION OF THE DRAWINGS

FIGS. 7(a) and (b) show the construction of a compact light source device according to an embodiment of the invention;

FIG. 8 shows the construction of a dot percentage meter used in combination with the embodiment of FIG. 7; and FIG. 9 shows how the dot percentage meter of FIG. 8 is used in combination with the light source of the embodiment of FIG. 7 and briefly illustrates their functional elements

EMBODIMENTS

First, the precision in measurement will be described which must be taken into consideration while measuring the optical density and dot percentage. The optical density D is given by:

$$D = -\log \frac{I}{If} = \log If - \log I \quad (1)$$

where I represents the quantity of transmitted light measured and If represents the quantity of transmitted light at a full scale. As will be described later, both log I and log If should be within the precision of ±0.005. Therefore, the precision in measurement for If and I is required to be within ±If/86 and ±I/86 respectively and the number of effective digits of the measured value is required to have a sufficient number.

The dot percentage A is given by:

$$A = (1 - I/If) \times 100 \quad (2)$$

As described later, since the precision suffices if a ratio I/If is within a precision of ±0.5%, the precision in measurement for If is required to have ±If/200 and for I to have a constant value of ±If/200 regardless of the magnitude of a measured value. Therefore, in measuring the dot percentage, a finer or narrower range is required than that in measuring the optical density. However, in measuring the dot percentage, there is required only a zero adjustment, i.e., only an adjustment of a full scale range.

Figure 1:
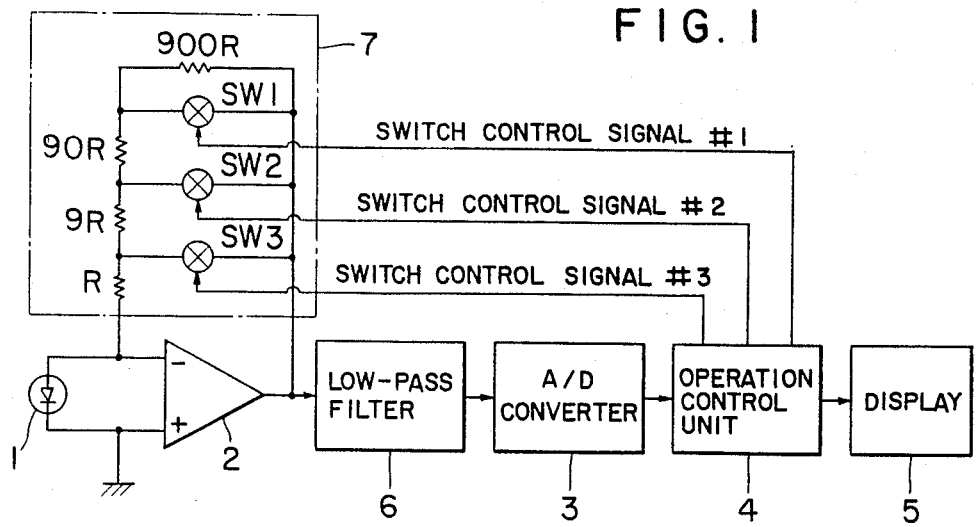
FIG. 1 schematically shows an example of a circuit of an optical density/dot percentage measuring device according to the present invention.

FIG. 1 shows one example of a circuit arrangement of the optical density and dot percentage measuring device according to the present invention. First, the function of the optical density measuring device will be explained. In this embodiment, the optical density measuring device comprises: a semiconductor photoelectric conversion element 1 such as a photodiode photoelectrically converting a transmitted light or reflected light of an object to be measured into a photocurrent; an operational amplifier 2 for converting the photocurrent into a voltage and amplifying the voltage a low-pass filter 6 for cutting off an AC component of the voltage signal from the operational amplifier 2; an A/D converter 3 for converting an analog voltage signal from the filter 6 into a digital signal; an operation control unit 4 including such as a microcomputer for outputting switch control signals #1 to #3 and a data signal; and a display 5 for displaying the data from the operation control unit 4. The switch control signals #1 to #3 control the on/off of analog switches SW1 to SW3 based upon the digital signal from the A/D converter 3 and in accordance with the automatic range control method of the invention which will be described later. The data signal is indicative of data to be displayed and obtained by converting the digital signal from the A/D converter 3. In addition, a gain switching circuit 7 is provided wherein a plurality of feedback resistors R, 9R, 90R and 900R are connected in series between the input and output terminals of the operational amplifier 2, and the analog switches SW1 to SW3 are respectively connected between the output terminal of the operational amplifier and the respective interconnections of 900R and 90R, 90R and 9R, and 9R and R. A programmable gain amplifier whose gain is controlled by the operation control unit 4 is connected, if necessary, between the low-pass filter 6 and A/D converter 3. The operation of the analog switches SW1 to SW3 is controlled in accordance with Table 1 described later. With the arrangement as above, the number of analog switches is reduced to 3 as compared with 4 in case of the prior art analog switches.

TABLE 1

|  | SW1 | SW2 | SW3 |
|---|---|---|---|
| × 1000 | OFF | OFF | OFF |
| × 100 | ON | OFF | OFF |
| × 10 | X | ON | OFF |
| × 1 | X | X | ON |

In Table 1, symbol X indicates that both on or off may be used.

In the embodiment, the low-pass filter 6 is inserted after the operational amplifier 2. This leads to the use of a common light table instead of a light source such as a halogen lamp powered with a constant voltage source as in the conventional fixed mount type optical intensity measuring device. Conventionally, if a common light table is used as a light source, disadvantages are that (1) flicker components of a frequency 2 times as high as that of a drive power source are included in a measured signal and that (2) the quantity of light changes as the location of the light table moves. The low-pass filter 6 eliminates the above problem (1) and cuts off the AC components in a measured signal to make only its DC component as an object to be measured.

In this embodiment, to solve the above problem (2), a conventional, cumbersome full scale adjustment with hand through a variable resistor is not adopted, but the automatic range control method described later has been adopted, thereby enabling to perform a full scale adjustment at a short time. The automatic range control method of the present invention has solved the problem that: the provision of the low-pass filter 6 results in a long response time of a signal at the time of changing the measurement range (or gain) so that a wait time is necessary until data is stabilized and becomes suitable for A/D conversion. In particular, if 100 Hz flicker is desired to be reduced by 1/100 and a first order RC filter is used, of which the cut-off frequency is 1 Hz and time constant τ is 0.16 sec, then about 7τ or 1.12 sec is required until the output fluctuation caused by the range switching becomes within 1/1000 of the target value. 1/1000 here corresponds to the resolution of a 10 bit A/D converter. To reduce such delay, an automatic range control is desired which can respond quickly.

Figure 2:
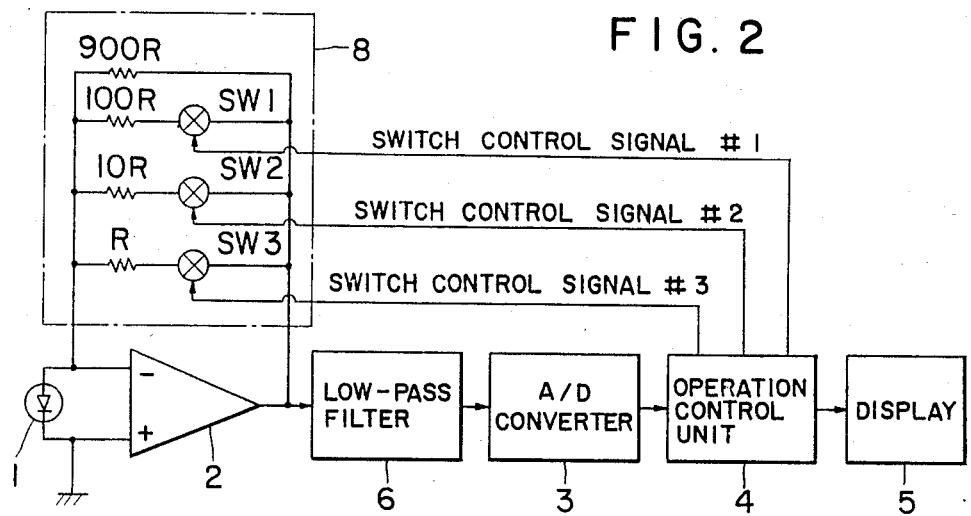
FIG. 2 schematically shows another example of the circuit of the optical density/dot percentage device.

FIG. 2 shows another example of a circuit arrangement of the optical density/dot percentage measuring device. This circuit arrangement is the same as with FIG. 1 except for gain switching circuit 8. In the gain switching circuit 8, a plurality of resistors R, 10R, 100R and 900R are connected in parallel between the input and output terminals of the operational amplifier 2. The resistors R, 10R and 100R are respectively connected in serial to respective analog switches SW1 to SW3. The operation of the analog switches SW1 to SW3 is controlled in accordance with Table 2. With the circuit arrangement as above, the number of analog switches is reduced to 3 as compared with 4 in the conventional analog switches.

TABLE 2

|  | SW1 | SW2 | SW3 |
|---|---|---|---|
| × 1000 | OFF | OFF | OFF |
| × 100 | ON | OFF | OFF |
| × 10 | X | ON | OFF |

TABLE 2-continued

| | SW1 | SW2 | SW3 |
|---|---|---|---|
| ×1 | X | X | ON |

Symbol X in Table 2 indicates that both on and off may be used.

Now, the automatic range control according to the present invention will be described. In a conventional automatic range control, measurement is first made at the widest range having a smallest amplification factor to check if the highest digit becomes other than zero. In case of zero, the range is switched one after another to a smaller or narrower range having a larger amplification factor. A measured value is determined from an A/D conversion value when the highest digit becomes for the first time other than zero and the range value, i.e., gain value at that time. In such a conventional automatic range control operation, the number of measurements until the ultimate measured value is obtained becomes 4 at its maximum, i.e., through the measurements at $\times 1 \rightarrow \times 10 \rightarrow \times 100 \rightarrow \times 1000$. Since one measurement takes more than 1.12 sec, the time required for completing the measurement becomes more than 4.48 sec, which is recognized as relatively long for an operator and poor in work efficiency.

In contrast with the above, according to the automatic range control method of the present invention, information obtained from the A/D converter is positively employed for reducing the overall measuring time. In the present invention, an A/D conversion is first made at $\times 1$ range by the 10 bit A/D converter. The A/D conversion value is compared with those values in Table 3 to determine a gain to be selected and perform further A/D conversion.

TABLE 3

| A/D Conversion Value | Gain to be Selected |
|---|---|
| 0–9 | Current Gain × 100 |
| 10–99 | Current Gain × 10 |
| 100– | Current Gain is proper |

If the current gain corresponds to a proper range, then the A/D conversion value at that time is used for an ultimate measured value. According to this method, 3 A/D conversions i.e., at the ranges $x1 \rightarrow \times 100 \rightarrow \times 1000$ suffice to select $\times 1000$ range, thus reducing the time required for measurement. Furthermore, if an overflow of the 10 bit A/D converter is adapted to be detected, the measurement may start from $\times 10$ range or from the range associated with a full scale. In this case, the range or gain is selected in accordance with Table 4.

TABLE 4

| A/D Conversion Value | Gain to be Selected |
|---|---|
| 0–9 | Current Gain × 100 |
| 10–99 | Current Gain × 10 |
| 100–999 | Current Gain is proper |
| 1000–Overflow | Current Gain/10 |

In Table 4, it is appreciated that the gain is reduced by 1/10 when an overflow of the A/D conversion value is detected. With such arrangement, if $\times 1000$ range is to be selected, only 2 A/D conversions, i.e. $\times 10$ range $\rightarrow \times 1000$ range suffice by starting the measurement from $\times 10$ range. Thus, the overall measurement time is reduced by half as compared with the prior art case.

The above gain selection can be described generally as in the following: a value Ii is solved from a value Vi obtained through A/D conversion at a given gain Gi based upon an equation $Ii = Vi/Gi$. Then, the following gain $Gi+1$ is selected in accordance with where the value Ii is included among the plurality of preset ranges in Table 5. If the selected gain $Gi+1$ coincides with the current gain Gi, then the value Ii ultimately becomes a measured value. If it does not coincide, a measurement is again performed at the gain $Gi+1$ and similar procedures are repeated until a coincidence is obtained. It is noted here that the value Ii is normalized by setting its maximum at "1". In setting the ranges for practical use, each range is set by overlapping with each other so as to avoid the gap between the ranges due to some errors in the values of the circuit elements.

TABLE 5

| Ii | Gi + 1 |
|---|---|
| 1–0.316 | × 1 |
| 0.316–0.1 | × 3.16 |
| 0.1–0.01 | × 10 |
| 0.01–0.001 | × 100 |
| 0.001–0 | × 1000 |

As a first gain G, the smallest gain ($\times 1$) or the gain associated with the measurement at full scale is used. If a gain ratio relative to each gain has the same value, it is unnecessary to calculate the value Ii, but the next gain $Gi+1$ is determined by multiplying the current Gi based upon the Vi value at the gain Gi.

For instance, the gain $Gi+1$ can be determined in accordance with Table 6.

TABLE 6

| Vi | Gi + 1 |
|---|---|
| Overflow | Gi/10 |
| 1–0.1 | Current Gain Gi |
| 0.1–0.01 | Gi × 10 |
| 0.01–0 | Gi × 100 |

If the value of gain calculated based upon Table 6 exceeds the predetermined maximum or minimum gain, either the maximum or minimum value is used.

Besides the above automatic range control method, there is another method to reduce the measurement time by increasing the order of the filter. For instance, instead of the first order low-pass filter, if a second order low-pass filter is used and intended to achieve the same attenuation characteristic as the first order RC filter at 100 Hz, then the cut-off frequency fc becomes 10 Hz and the time constant $\tau$ becomes 0.0225 sec. In this case, $7\tau$ becomes 0.157 sec so that the time required for measurement is reduced as compared with 1.12 sec as in the first order RC filter. This method of increasing the filter order in combination with the above automatic range control method enables a further reduction in the measurement time. Furthermore, in performing an automatic ranging, the measurement time is reduced by using as an initial range the range at a full scale adjustment.

Next, the function of the dot percentage measuring device will be described. There is no necessity to measure the dot percentage by using logarithm, and so a narrow measurement range is possible. Therefore, at a measurement after a full scale adjustment is completed, an A/D conversion is performed by fixing the corresponding range at the range associated with the full scale value. Thus, it is unnecessary to switch the range so that the measurement time is shorter than that in measuring the optical density. The precision of a full scale value in the measurement of a dot percentage, however, is required to have a higher precision than in the measurement of the optical density. In particular, the repetitive precision normally required in measuring the optical density is within ±0.01, while that required in measuring the dot percentage is within ±0.1%. To ensure such precision, the precision in measurement of the light quantity is required to be within ±0.005 in density measurement, while ±0.5% in dot measurement. The minimum count of 86 of the A/D conversion value (integer) of a quantity of light to be measured corresponds to ±0.005, while the minimum count of 200 corresponds to ±0.5%. The aforementioned minimum count of 86 is determined as follows. The 0.005 value of measurement precision corresponds to 1.0115 of transmissivity so that 0.0115 is obtained by operating (1.0115−1), and then 86 is obtained by dividing 1 by 0.0115. Another minimum count of 200 is determined by dividing 1 by 0.005 (0.5%). By the use of the 10 bit A/D converter, the maximum allowable gain ratio between the ranges becomes 1024/86=11.9 for the optical density and 1024/200=5.12 for the dot percentage. Therefore, the measuring ranges of a measuring device for both optical density and dot percentage measurements, must be arranged based upon the finer or narrower ranges, i.e., the dot percentage measurement. If so arranged, the number of ranges increases, for example, to ×1, ×3.162, ×10, ×31.62, ×100, ×316.2, ×1000. In such case, the adoption of only the above-mentioned automatic measurement range control circuit results in an increase of the number of resistors and analog switches to thereby complicate the circuit arrnagement.

Figure 3:
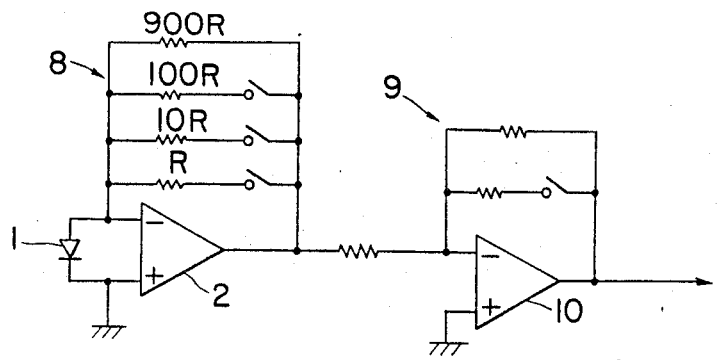
FIG. 3 is a circuit diagram showing a modification of the circuit.
Figure 4:
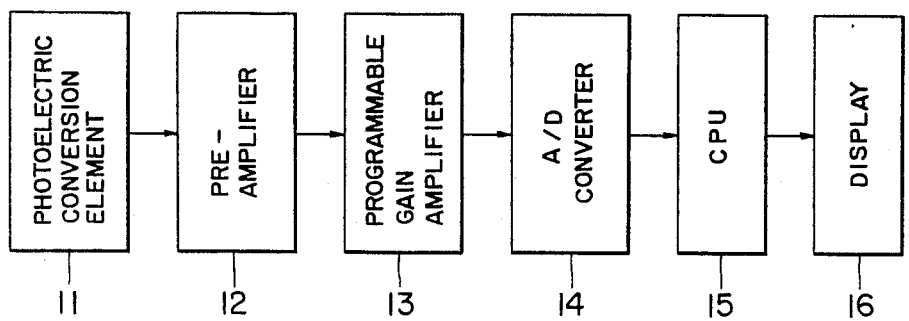
FIG. 4 is a block diagram showing an example of a conventional optical density measuring device.
Figure 5:
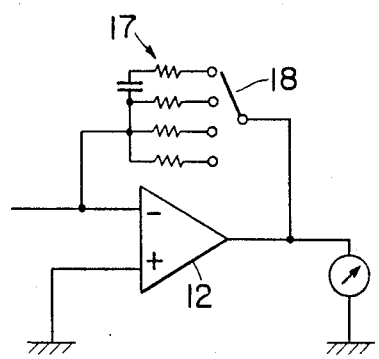
FIG. 5 is a circuit diagram showing an example of a conventional gain switching circuit.
Figure 6:
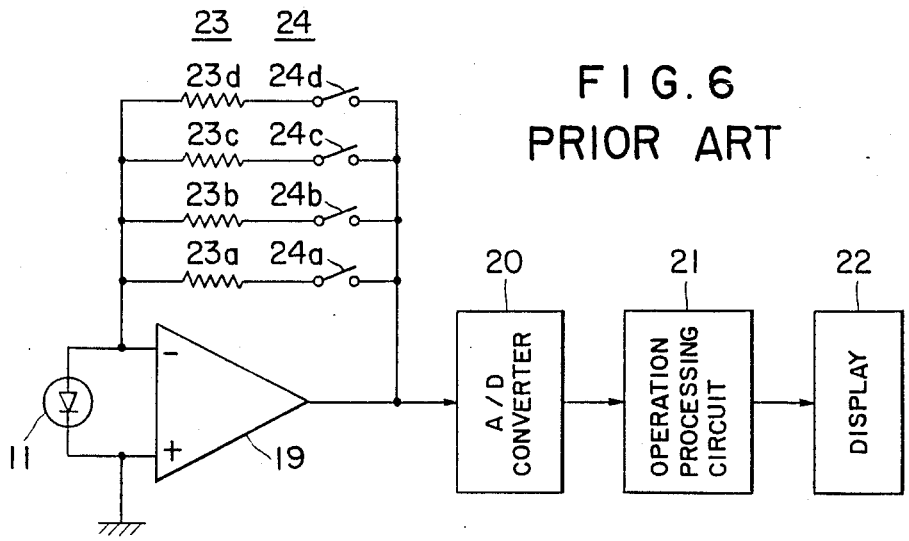
FIG. 6 is a circuit diagram showing a conventional optical density measuring device using the gain switching circuit of FIG. 5.

FIG. 3 shows one example of a substitutional circuit in consideration of the above problem. A programmable gain amplifier 10 is connected in series after the operational amplifier 2 and two amplifiers in total are used for constituting the range switching circuits. With this arrangement, the number of resistors and analog switches at the first stage range switching circuit need not be increased, as compared with the range switching circuit made of only the operational amplifier 2. In the present embodiment, the measurement ranges are divided into ×1, ×10, ×100, ×1000 at the first stage range switching circuit and into ×1, ×3.16 at the second stage range switching circuit. The switching ranges of the first stage range switching circuit cover a wide range, i.e., ×1 to ×1000, while the ranges of the second stage range switching circuit cover a narrow range, i.e., ×1 to ×3.162. Therefore, there is no problem that an off-set voltage at the preceding stage is amplified to a great degree. The second stage range switching circuit and the operational amplifier may accordingly be any types of operational amplifiers commonly used in the art. Furthermore, as the operational amplifier constituting the lowpass filter, the operational amplifier of the range switching circuit may be used in common. If zero adjustment is performed only for ×1 and ×3.162 ranges, the whole ranges are set such that only those ranges having a small gain are finely set, while those ranges having a large gain are set coarsely to make the number of ranges small, to decrease leakage current and improve the measurement precision. In this case, the range switching circuit may be made of a single stage.

The optical density D is solved, in accordance with the following equations from the measured value (gain) G and A/D conversion value V obtained as above:

$$\text{Transmissivity } T = (Gf \times V)/(Vf \times G) \quad (3)$$

$$\text{Optical density } D = -\log T \quad (4)$$

where Gf and Vf represent the gain at a full scale and the measured value of an A/D conversion value, respectively, and G and V represent the measured values of the quantity of transmitted light.

As described above, according to the control method of the present invention, the number of selections of measurement ranges can be reduced, and the precision in measurement can be improved.

The dot percentage A is obtained by the following equation:

$$\text{Dot percentage } A = (1-T) \times 100(\%) \quad (5)$$

It is easy to perform the above operations and display the operation result by using such as a microcomputer. Furthermore, as disclosed in Japanese Unexamined Patent Publication No. 55-27909, compensation for the fringe and ghost of dots can readily be performed by using such as a microcomputer.

The advantageous effect of the present invention is as follows:

(1) A compact and portable optical density/dot percentage measuring device can be realized.

(2) A common light table can be used as a light source. Furthermore, a measurement can be carried out at a high precision even under the conditions such as light source flicker due to the commercial power source frequency or variation of light quantity due to a change of measuring location.

(3) The provision of a specific automatic range control method enables a reduction of the number of selections of measurement ranges and improvement of the precision in measurement.

FIGS. 7(a) and (b) show the construction of the light source device according to an embodiment of the present invention, wherein FIG. 7(a) is a perspective view as seen from the front side and FIG. 7(b) is a perspective view as seen from the rear side. The compact light source device has a measurement table section 112 on the upper side of a main body 111. A film to be measured is placed on the measurement table 112. At a corner of the measurement table 112, an illumination section 113 is provided on which a circle of 10 mm diameter is depicted as a measurement mark. Light from a built-in light source is applied toward the measurement mark. A switch 114 is provided for turning on and off the built-in light source.

A dot percentage meter housing X and a light source housing Y are formed at the rear side of the main body 111. The dot percentage housing X has a space into which the dot percentage meter can be inserted. The wall partially defining the space is provided with a rail 111A which fits with a groove formed in the casing of the dot percentage meter. A projection 111B is also formed on the wall, the projection being so made to engage with a concavity formed in the casing of the dot percentage meter and prevent the meter from sliding out of the main body 111. The mutual position between the projection and the concavity may be reversed. The light source housing Y accommodates a battery, lamp, reflecting plate, diffusing plate and so on, and is adapted to replace the battery or others by removing a lid 115.

FIG. 8 shows an outer appearance of a dot percentage meter to be combined with the compact light source device 111 of FIG. 7. The case comprises a bottom case 121, top case 122 and battery lid 123.

The bottom case 121 is formed with a groove 121A and a concavity 121B, respectively engaging with the rail 111A and projection 111B of the main body 111 of the device. In cooperative association with these elements, the compact light source device 110 and dot percentage meter 120 are fixed to each other. Reference 124 represents a detection unit for introducing measuring light.

The top case 122 is provided with a display window through which the measured result is displayed, main switch 26 and other various switches 127, 128. A battery lid 123 has no elements mounted thereon to be operated.

FIG. 9 shows how the measurement is carried out by using the compact light source 110 shown in FIG. 7 and the dot percentage meter 120 shown in FIG. 8. The switch 114 of the compact light source 110 is turned on to connect the battery and the lamp 116. Light from the lamp is applied to the diffusing plate 118 through a scattering reflecting plate 117 of a matte finish to form uniform light. By virtue of the reflecting plate 117 constructed as above, an effective distance between the lamp and the diffusing plate can be made long to thereby reduce the influences of such as distortion of the reflecting mirror surface.

The light is applied to a film 130 placed on the measurement table 112 (FIG. 7) of the compact light source device 110.

Light transmitted from the film 130 is then introduced to the detection unit 124 of the dot percentage meter 120 to photoelectrically detect the light with a sensor 129 and thereafter amplify the signal at an amplifier AMP. Then, the amplified signal is converted into a digital signal at an A/D converter which digital signal is then converted at a CPU into a display signal to send it to a display 125.

By using the compact light source 110 and dot percentage meter 120, the illumination section 113 (FIG. 7) of the dot percentage meter 120 is aligned with the detection unit 124 of the dot percentage meter 120. In this case, the dot percentage meter 120 can be properly placed upon the compact light source device 110 so that work efficiency is good and the film 130 can be sandwiched suitably therebetween. In the alignment of the dot percentage meter 120, the groove 121A fits the operator's finger so the meter can be handled with ease. Furthermore, the position alignment can be readily performed by looking at the measurement mark which is of a relatively large dimension.

In the above embodiment, the dot percentage meter has been employed as a measuring device. However, other common measuring devices incorporating transmission light, such as transmission density meters, are also applicable.

As described above, the compact light source device of the present invention is so constructed as to be compatible with the previously developed dot percentage meter, so that the functions of the dot percentage meter may be fully utilized. This means that the light source device is advantageous not only to the measurement, but it is very useful in that the outer dimension is very small when the dot percentage meter is housed in the light source device during transportation.

What is claimed is:

1. An automatic range control method for an optical density/dot percentage measuring device, comprising:

a photoelectric conversion element for photoelectrically converting a transmitted or reflected light of an object to be measured into a photocurrent;

an operational amplifier for converting said photocurrent into a voltage signal for amplifying said voltage signal;

a low-pass filter for cutting off an AC component of said voltage signal from said operational amplifier;

an A/D converter for converting said voltage signal from said low-pass filter from an analog value into a digital value;

an operation control unit for outputting, in response to said digital signal, switch control signals for the control of an on/off state of a plurality of analog switches and display data; and a gain switching circuit having a plurality of feedback resistors and said analog switches connected between the input and output terminals of said operational amplifier for switching a plurality of measurement ranges;

wherein said operation control unit outputs said switch control signals to said gain switching circuit in such a manner that said operation control unit calculates a value $Ii = Vi/Gi$ based upon a value $Vi$ obtained through said A/D conversion of said voltage signal at a given gain $Gi$, selects a gain $Gi+1$ based upon which range of said plurality of mesurement ranges corresponds to said value $Ii$; and if the gain $Gi+1$ coincides with the current gain $Gi$, said value $Ii$ is made a fixed value, while if the gain $Gi+1$ does not coincide with the current gain $Gi$, then a value $Vi+1$ is obtained through an A/D conversion of the measured value at the gain $Gi+1$ to calculate a value $Ii+1 = (Vi+1)/(Gi+1)$, and similar procedures are repeated until a coincidence is obtained.

2. An automatic range control method for an optical density/dot percentage measuring device according to claim 1, wherein the width of a measurement range is finally set at a range associated with a full scale measurement, and the width of a measurment range is set coarsely at other measurement ranges.

3. An automatic range control method for an optical density/dot percentage measuring device according to claim 1, wherein said plurality of measurement ranges are set according to a decimal ratio and are reselected when the value $Vi$ varies.

4. An optical density/dot percentage measuring device, comprising:

a photoelectric conversion element for photoelectrically converting a transmitted or reflected light of an object to be measured into a photocurrent;

an operational amplifier for converting said photocurrent into a voltage signal for amplifying said voltage signal;

a low-pass filter for cutting off an AC component of said voltage signal from said operational amplifier;

an A/D converter for converting said voltage signal from said low-pass filter from an analog value into a digital value;

an operation control unit for outputting, in response to said digital signal, switch control signals for the control of an on/off state of a plurality of analog switches and a data signal representative of data to be displayed;

a display for displaying said data; and a gain switching circuit having a plurality of feedback resistors connected in parallel between the input and output terminals of said operational amplifier, said analog switches being respectively connected to each of said feedback resistors except the one of said feedback resistors having the largest resistance value.

5. An optical density/dot percentage measuring device according to claim 4, wherein a programmable gain amplifier is connected after said gain switching circuit and said operational amplifier.

6. An optical density/dot percentage measuring device according to claim 4, wherein in said gain switching circuit, the width of a range is finely set at a range associated with a full scale measurement, and the width of a range is set coarsely at other measurement ranges.

7. An optical density/dot percentage measuring device comprising: a photoelectric conversion element for photoelectrically converting a transmitted or reflected light of an object to be measured into a photocurrent; an operational amplifier for converting said photocurrent into a voltage signal for amplifying said voltage signal; a low-pass filter for cutting off an AC component of said voltage signal from said operational amplifier; an A/D converter for converting said voltage signal from said low-pass filter from an analog value into a digital value; an operation control unit for outputting, in response to said digital signal, switch control signals for the control of an on/off state of a plurality of analog switches and a data signal representative of data to be displayed; a display for displaying said data; and a gain switching circuit having a plurality of feedback resistors connected in series between the input and output terminals of said operational amplifier, said analog switches being respectively connected between the terminals of said feedback resistors except that connected to the input terminal of said operational amplifier, and the output terminal of said operational amplifier.

8. An optical density/dot percentage measuring device according to claim 7, wherein a programmable gain amplifier is connected after said gain switching circuit and said operational amplifier.

9. An optical density/dot percentage measuring device according to claim 7, wherein in said gain switching circuit, the width of a range is finely set at a range associated with a full scale measurement, and the width of a range is set coarsely at other measurement ranges.

* * * * *